(12) United States Patent
Anitua Aldecoa

(10) Patent No.: US 10,376,194 B2
(45) Date of Patent: Aug. 13, 2019

(54) DEVICE FOR THE COLLECTING OF BLOOD OR A BLOOD COMPOUND

(71) Applicant: BIOTECHNOLOGY INSTITUTE, I MAS D, S.L., Vitoria (Alava) (ES)

(72) Inventor: Eduardo Anitua Aldecoa, Vitoria (ES)

(73) Assignee: BIOTECHNOLOGY INSTITUTE, I MAS D, S.L., Vitoria (Alava) (ES)

( * ) Notice: Subject to any disclaimer, the term of this patent is extended or adjusted under 35 U.S.C. 154(b) by 350 days.

(21) Appl. No.: 15/171,318

(22) Filed: Jun. 2, 2016

(65) Prior Publication Data

US 2016/0354020 A1    Dec. 8, 2016

(30) Foreign Application Priority Data

Jun. 3, 2015 (ES) .................................. 201530776

(51) Int. Cl.
| | | |
|---|---|---|
| *G01N 1/24* | (2006.01) |
| *A61B 5/15* | (2006.01) |
| *G01N 1/14* | (2006.01) |
| *A61B 5/154* | (2006.01) |
| *B01L 3/00* | (2006.01) |

(52) U.S. Cl.
CPC .... *A61B 5/150099* (2013.01); *A61B 5/15003* (2013.01); *A61B 5/154* (2013.01); *A61B 5/150236* (2013.01); *A61B 5/150244* (2013.01); *A61B 5/150351* (2013.01); *A61B 5/150908* (2013.01); *B01L 3/50825* (2013.01);
(Continued)

(58) Field of Classification Search
CPC ................ A61M 1/0009; A61B 5/154; A61B 5/150351; B01L 3/14; B01L 3/50; G01N 2001/248; G01N 2001/2071–2085; G01N 33/50; G01N 33/5002; F04B 37/00

USPC ................. 600/573, 577; 604/228
See application file for complete search history.

(56) References Cited

U.S. PATENT DOCUMENTS

| | | | | |
|---|---|---|---|---|
| 3,147,753 A | * | 9/1964 | Nogier ..................... | A61M 3/00 604/222 |
| 3,645,253 A | * | 2/1972 | Goverde .......... | A61B 5/150251 600/578 |
| 3,782,197 A | * | 1/1974 | Grams ..................... | G01N 1/14 73/864.23 |
| 3,885,549 A | * | 5/1975 | Green ................ | A61B 5/15003 600/573 |

(Continued)

FOREIGN PATENT DOCUMENTS

| | | |
|---|---|---|
| EP | 2077115 A1 | 7/2009 |
| EP | 2829288 A1 | 1/2015 |

(Continued)

*Primary Examiner* — Peter J Macchiarolo
*Assistant Examiner* — Alexander A Mercado
(74) *Attorney, Agent, or Firm* — Browdy and Neimark, PLLC

(57) ABSTRACT

A device for the extraction of blood or a blood compound is provided that includes a tube, a piston assembly, a handle assembly that can be clipped to the piston assembly, and a perforable sealing element that prevents the flow of fluid from a sealed interior space of the tube towards a longitudinal interior cavity of the handle assembly located adjacent to a separable area of the handle assembly. In use, the handle assembly is pushed to the bottom of the tube, causing the handle assembly to be clipped to the piston assembly, the handle assembly and the piston assembly are then moved rearwards forming a vacuum in the space, the piston assembly is clipped to an end cap of the tube and the gripping portion of the handle assembly is separated, obtaining a vacuum container with a perforable closure.

21 Claims, 15 Drawing Sheets

(52) U.S. Cl.
    CPC ........ *G01N 1/14* (2013.01); *B01L 2200/0689* (2013.01); *B01L 2200/141* (2013.01); *B01L 2300/045* (2013.01)

(56) References Cited

U.S. PATENT DOCUMENTS

| | | | | |
|---|---|---|---|---|
| 4,133,863 | A * | 1/1979 | Koenig | A61B 5/15003 422/50 |
| 4,632,672 | A * | 12/1986 | Kvitrud | A61B 5/150236 604/222 |
| 4,730,624 | A * | 3/1988 | Waters | A61B 5/15003 600/577 |
| 5,632,396 | A * | 5/1997 | Burns | B01L 3/50825 215/247 |
| 6,126,643 | A | 10/2000 | Vaillancouert | |
| 6,186,960 | B1 * | 2/2001 | Tripp | A61B 5/15003 600/576 |
| 2002/0156396 | A1 * | 10/2002 | Tiu | A61M 5/322 600/576 |
| 2011/0083978 | A1 | 4/2011 | Lavi | |
| 2011/0224610 | A1 * | 9/2011 | Lum | A61M 5/38 604/125 |
| 2014/0010740 | A1 * | 1/2014 | Anitua Aldecoa | A61B 5/1433 422/570 |

FOREIGN PATENT DOCUMENTS

| | | |
|---|---|---|
| WO | 88/06861 | 9/1988 |
| WO | 2006058435 A2 | 6/2006 |
| WO | 2014006238 A1 | 1/2014 |

* cited by examiner

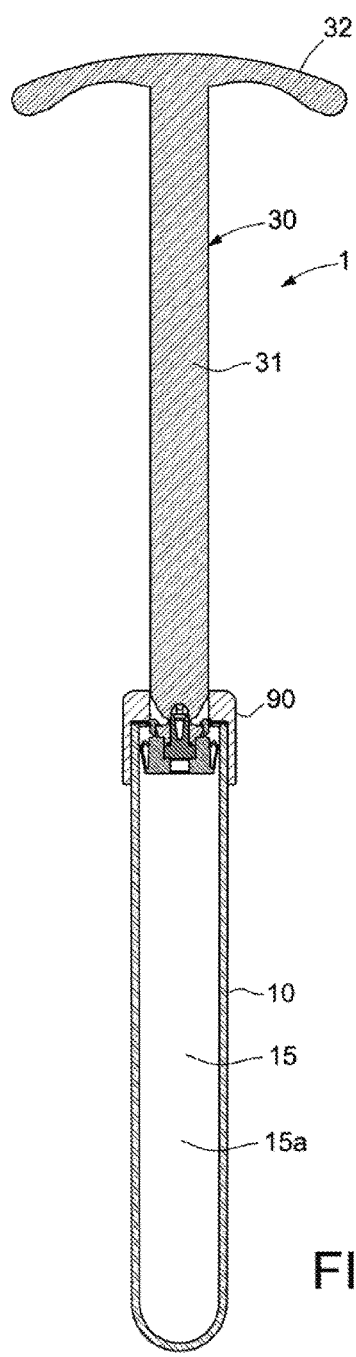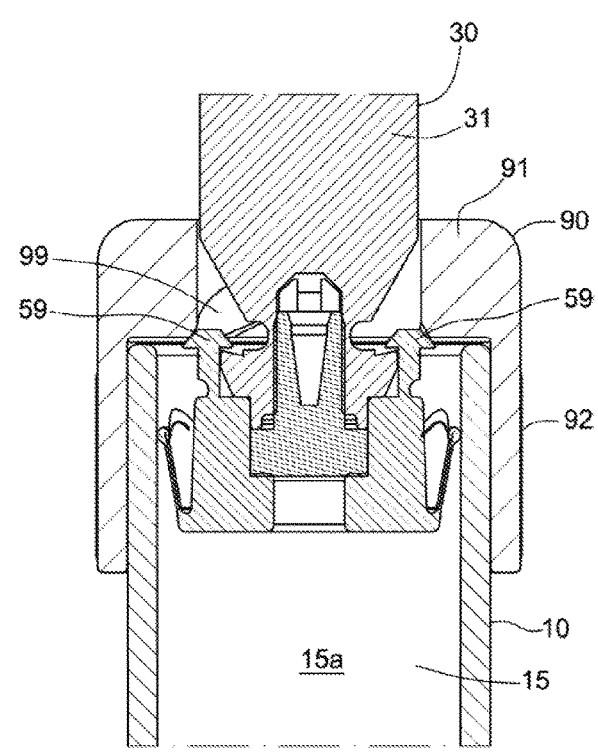
FIG.13
FIG.14

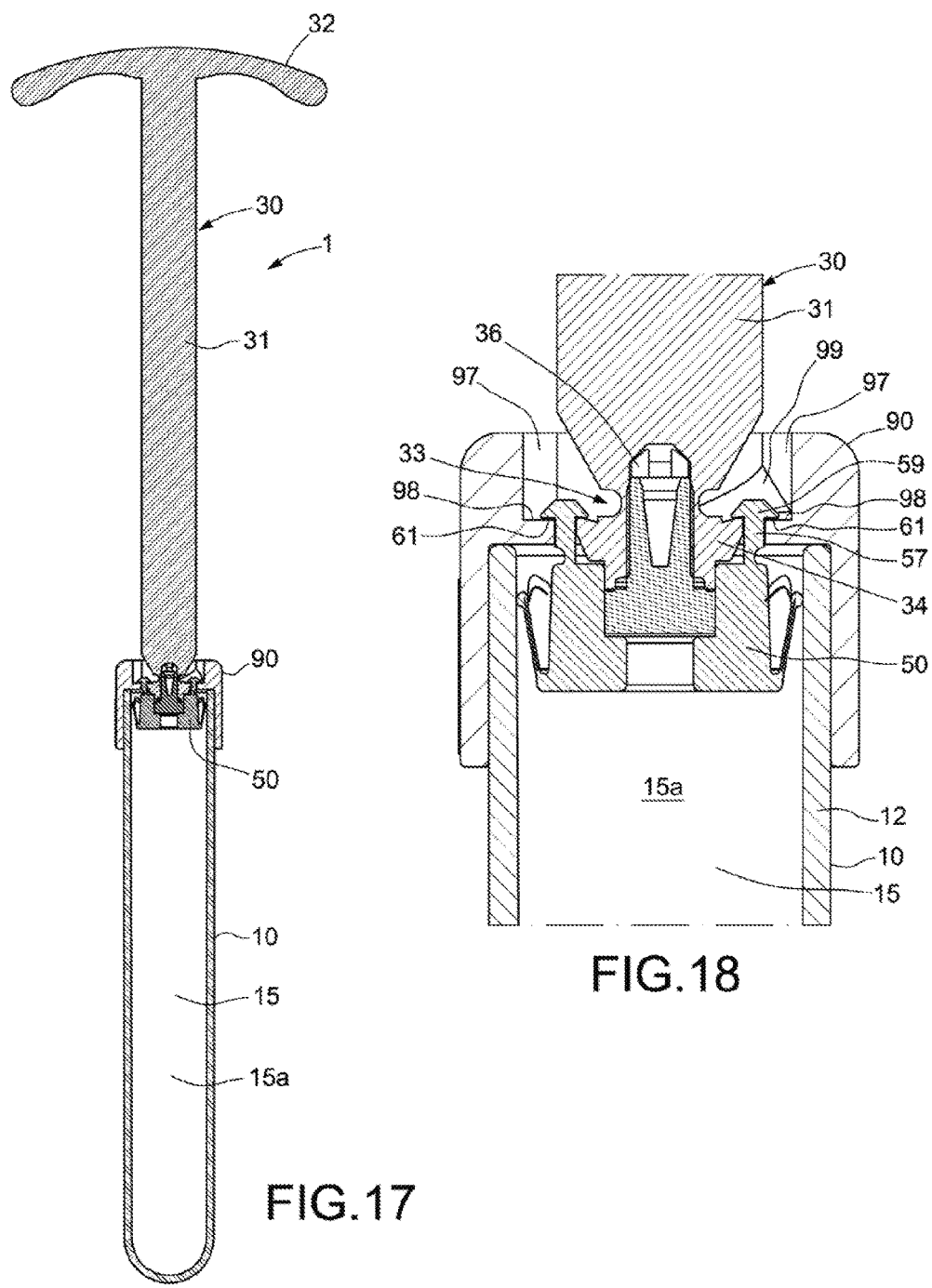

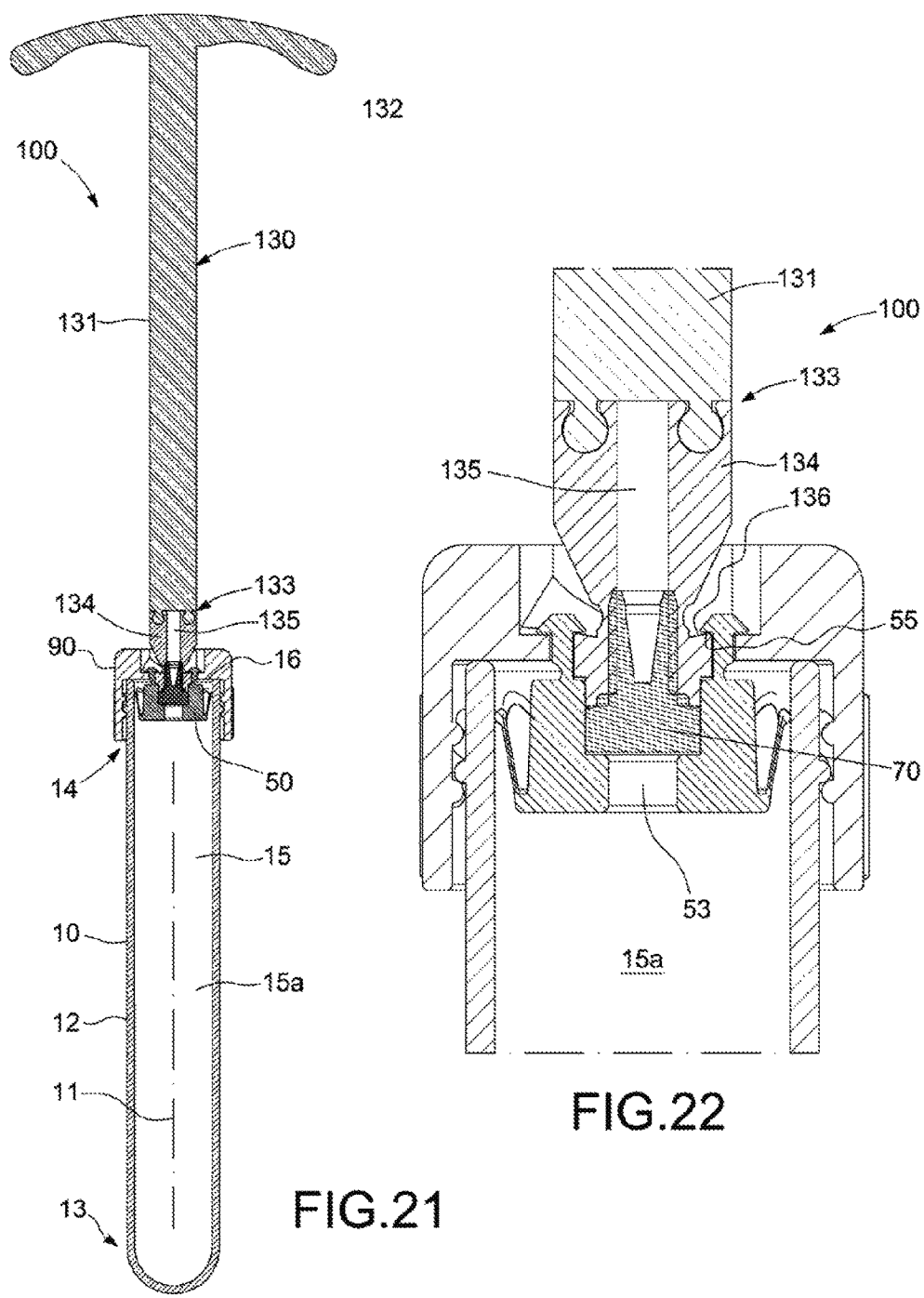

DEVICE FOR THE COLLECTING OF BLOOD OR A BLOOD COMPOUND

FIELD OF THE INVENTION

The invention relates to a device for the collecting of blood or a blood compound by suction or vacuum, and more specifically, to a device that has a tube, a piston assembly and a detachable handle for creating a vacuum in the tube just before using the device, ensuring optimum vacuum conditions when using the device, for example, to receive blood extracted from a patient.

PRIOR ART

To draw blood from humans or animals, sealed vacuum tubes are generally used. A sealed tube is a tube having an interior atmosphere pressure that is lower than the pressure of the blood in the veins. Normally, the tubes are closed using a cap or a perforable seal, such as a septum. Blood is removed by inserting a hypodermic needle into the vein or artery of the person or animal. This needle is linked to an opposing needle, which in turn pierces the seal of the tube and is inserted inside the vacuum tube. Once the vein or artery is communicated with the inside of the tube, blood is removed as a result of the pressure difference between the vein or artery and the tube. The extraction is finalized by removing the needle from the body.

Vacuum tubes used to remove blood have a simple configuration; they are formed as an elongated receptacle which is closed at one end by the aforementioned perforable seal, and which has a factory-created vacuum, i.e. a vacuum provided during their manufacture. Normally, health centres or organisations are supplied with a large number of tubes that are stored and only used when necessary. Unfortunately, the capacity of the receptacles and perforable seals to maintain the vacuum created at the factory is limited, as the tubes gradually lose their optimum vacuum conditions over time through unions between pieces and even through the tube walls. To prevent the loss of vacuum, tubes may be manufactured having a greater thickness and/or with components that provide a tighter seal, which leads to an increase in the manufacturing cost of the tubes. It is also possible to somewhat slow down the vacuum loss by storing the tubes under very precise temperature conditions. However, even if they are made out of better materials and tighter unions, and even stored under optimum conditions, the tubes cannot avoid losing their aspiration capacity over time. Because of this, they have a limited useful life, i.e. they expire.

The aim of the present invention is to provide a blood extraction tube that offers optimum vacuum conditions right when it is to be used, and also presents a reasonable cost so that it becomes a viable alternative to the vacuum tubes currently used.

BRIEF DESCRIPTION OF THE INVENTION

An object of the present invention is a device for the collecting of blood or a blood compound, which can be manipulated at the time of use to create a depression or vacuum inside the tube, and which, once the vacuum has been created, presents a final shape that is analogous to that of a conventional tube so that it can be used in standard or conventional medical systems and apparatus (e.g., centrifugal machines, support grates and pipetting, etc.) without the need for specific accessories for its use. The device has a highly effective yet simple configuration, which enables a disposable tube to be manufactured at an affordable cost.

The device as per the invention comprises a tube, a handle assembly, a piston assembly and a perforable sealing element. The tube extends along a longitudinal axis and has a lateral wall, a closed distal end, a proximal end opposite the distal end, and an interior cavity communicated with the exterior by an opening at the proximal end. The piston assembly can move along the interior cavity of the tube, in contact with the lateral wall of the tube, and has at least one interior clipping surface and a longitudinal interior cavity. The piston assembly delimits a space between the piston assembly and the distal end of the tube. The handle assembly, in turn, has a gripping portion, a separable area (e.g., a breakable area, a detachable area, or a clipped area which can be unclipped) and an end portion that extends from this separable area. The end portion has a longitudinal interior cavity and at least one clipping surface. The end portion of the handle assembly can be moved with respect to the piston assembly to a position in which at least one clipping surface of the end portion comes into contact with an interior clipping surface of the piston assembly preventing the extraction of the end portion of the piston assembly. In this position, the perforable sealing element prevents the flow of fluid from the space between this piston assembly and the distal end of the tube towards the longitudinal interior cavity of the end portion of the handle assembly. Furthermore, in this position, the gripping portion of the handle assembly is accessible from the exterior of the device. In this clipping position, the user can therefore move the unit consisting of the handle assembly, the piston assembly and the perforable sealing element rearward to a position closer to the proximal end of the tube, creating a depression in the tube as a result of the rearward movement of the piston assembly and the subsequent increase in the volume of the space between the piston assembly and the distal end of the tube. Then, the user can separate and remove a significant part of the handle assembly, obtaining a vacuum-sealed tube with a seal that is both fluidtight and perforable by a needle.

Because the container of the present invention allows the vacuum to be created right before use, optimum vacuum conditions are available at the time of using the container without the need for the container to be made out of costly materials or stored under strict temperature conditions. It has been verified that, if the container of the present invention is manufactured using habitual, reasonably priced materials, optimum vacuum conditions are able to last the time required to carry out common applications involving the use of blood extracted from the human or animal body (e.g., 1, 2 or more hours).

The device in the present invention is also advantageous in that it only has one open end fitted with closure parts (the proximal end of the tube). This enables higher centrifugal pressures to be exerted, as the centrifugal force acts on the distal, hemispherical end of the tube, which does not have any continuity solution.

BRIEF DESCRIPTION OF THE FIGURES

The details of the invention can be seen in the accompanying figures, which do not intend to limit the scope of the invention:

FIG. 13 shows a cross-sectional view of the device of FIG. 1 in a fifth situation, in which the handle assembly has been pulled rearwards, causing the handle assembly, piston assembly and perforable sealing element to move rearwards, generating a depression inside the tube.

FIG. 14 shows an enlarged view of the piston assembly, the perforable sealing element, the end portion of the handle assembly and the cap in the situation of FIG. 13.

FIG. 17 shows a cross-sectional view of the device of FIG. 1 in a sixth situation, in which the handle assembly has been pulled rearwards and the handle assembly has been turned in a clockwise direction, causing the piston assembly to clip to the cap.

FIG. 18 shows an enlarged view of the piston assembly, the perforable sealing element, the end portion of the handle assembly and the cap in the situation of FIG. 17.

FIG. 21 shows a cross-sectional view of a second embodiment of the device as per the invention, in which the handle assembly has a clipped separable area, the device being shown in a similar situation to that of FIG. 17, i.e. with the handle assembly pulled rearwards and turned in a clockwise direction causing the piston assembly to clip to the cap.

FIG. 22 shows an enlarged view of the piston assembly, the perforable sealing element, the separable area and end portion of the handle assembly, and the cap in the situation of FIG. 21.

DETAILED DESCRIPTION OF THE INVENTION

The invention relates to a device for the collecting of blood or a blood compound by suction or vacuum, and more specifically, to a device having a tube, a piston assembly and a separable handle assembly for creating a vacuum in the tube just before using the device, ensuring optimum vacuum conditions when using the device, for instance, to draw blood from a patient.

Figure 1:
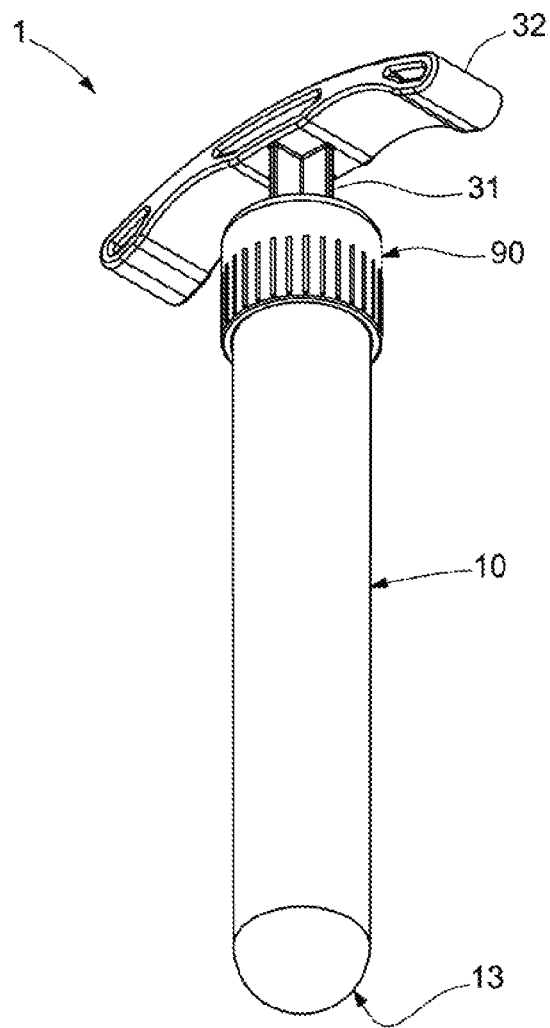
FIG. 1 shows a perspective view of an example of a device for the collecting of blood or a blood compound as per the invention.

FIGS. 1 to 20 show an illustrative embodiment of the device. In particular, FIG. 1 presents an exterior perspective view of the device (1), shown assembled. In turn, FIG. 2 shows an exploded perspective view of the device (1), enabling the different components to be illustrated.

Figure 2:
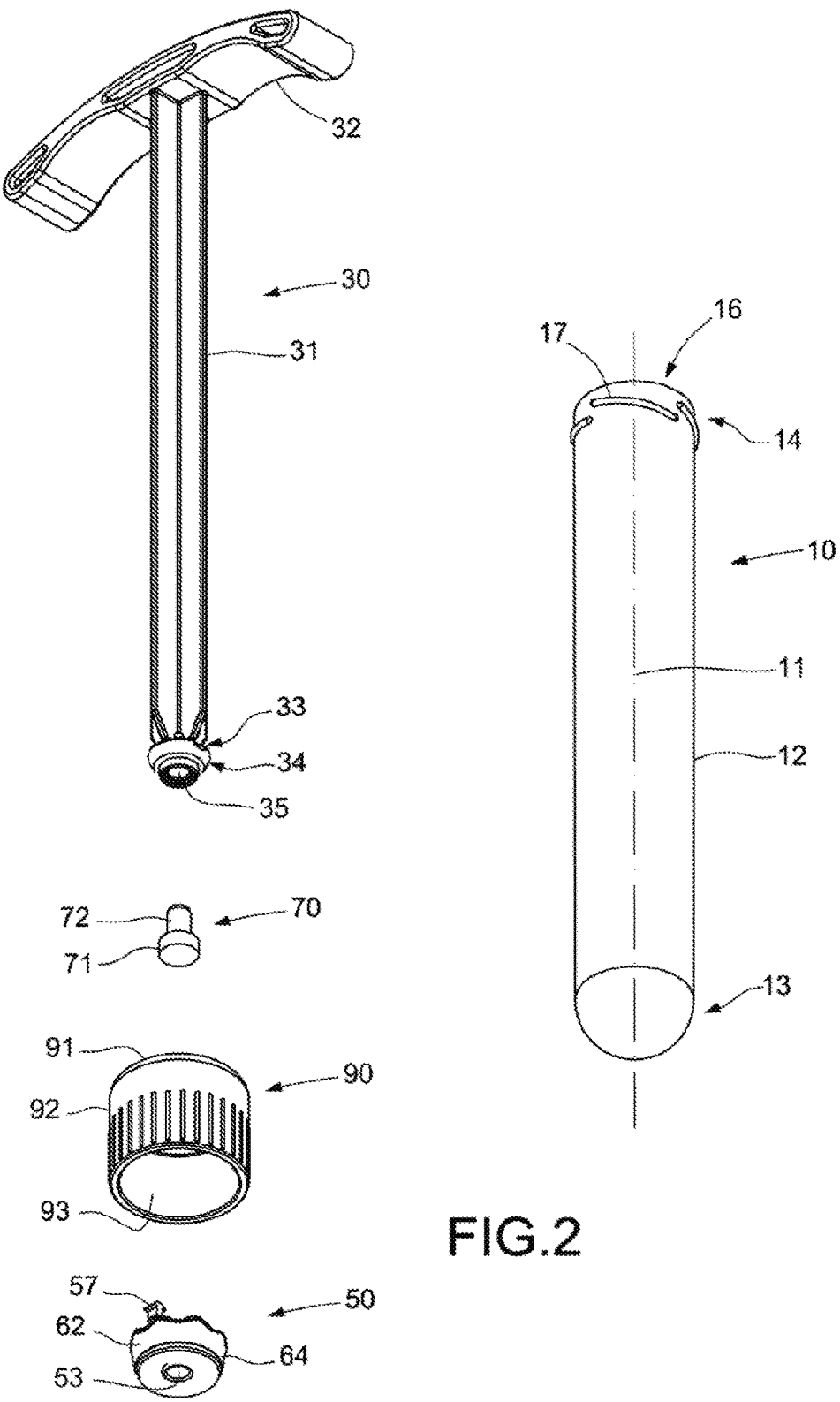
FIG. 2 shows an exploded view of the device of FIG. 1, showing the tube, the handle assembly, the perforable sealing element, the piston assembly and the cap.

It can be seen in FIG. 2 that the device (1) of the present embodiment comprises a tube (10), a handle assembly (30), a piston assembly (50), a perforable sealing element (70) and a cap (90).

Figure 7:
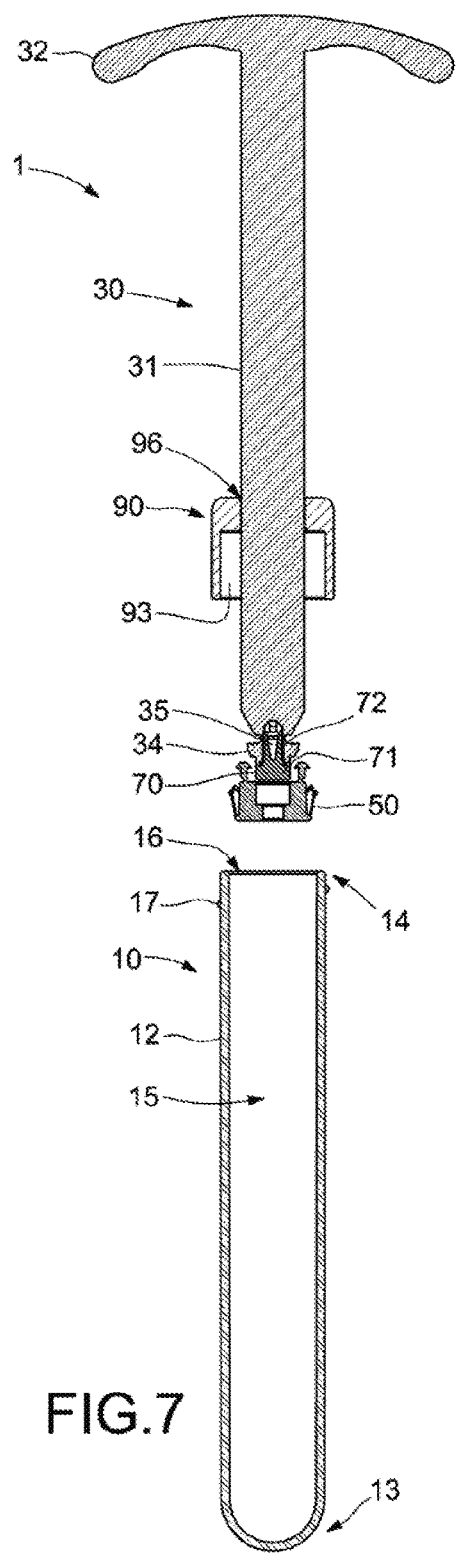
FIG. 7 shows a cross-sectional view of the device of FIG. 1 in an initial, pre-assembly situation.

The tube (10) extends along a longitudinal axis (11) and has a lateral wall (12), a distal end (13), a proximal end (14) opposite to the distal end (13), and an interior cavity (15) that is not shown in this figure. FIG. 7 shows a cross-sectional view of the tube (10) revealing the cavity (15), which is linked to the exterior of the tube (10) by an opening (16) located at the proximal end (14). The distal end (13) of the tube is closed. Preferably, the tube (10) is made out of a single piece and material, such as glass or injected plastic, so that the walls of the distal end (13) are a continuation of the lateral wall (12).

Figure 3:
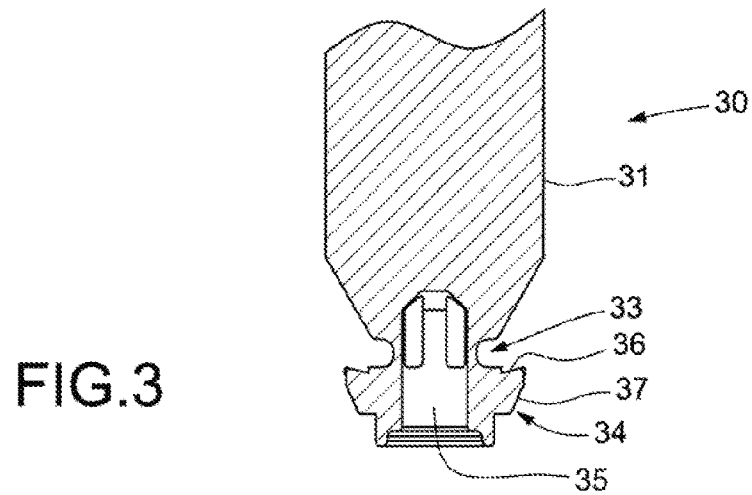
FIG. 3 shows a cross-sectional view of the end of the handle assembly of FIG. 2 in which the end portion and the separable area are located.

The handle assembly (30), as shown in FIG. 2, has an elongated body (31) and a gripping portion (32) or handle, which is arranged at one end of the elongated body (31) and forms a T with the elongated body (31) in the embodiment depicted herein. The handle assembly (30) also comprises a separable area (33), and an end portion (34) that extends from the separable area (33) in the opposite direction to the gripping portion (32) (i.e. to the end of the elongated body (31) opposite to the gripping portion (32)). The end portion (34) has a longitudinal interior cavity (35). FIG. 3 shows an enlarged view of the end of the handle assembly (30), allowing to more clearly appreciate the separable area (33), which is formed as a narrowed section or indentation carried out between the elongated body (31) and the end portion (34). In the embodiment shown here, the separable area (33) is breakable. In other words, it is possible to separate the gripping portion (32) of the handle assembly (30) from the end portion (34) of the handle assembly (30) by breaking the separable area (33) of the handle assembly (30). The end portion (34) of the handle assembly (30) includes at least one clipping surface (36), configured to be clipped to the piston assembly (50) as will be explained herein, and at least one oblique lateral surface (37) which widens towards the clipping surface (36), which contributes to causing the clipping. The lateral surface (37) may be conical, curved or a combination thereof.

Figure 6:
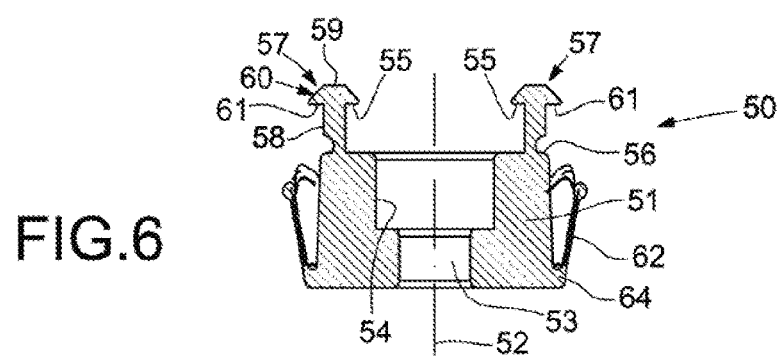
FIG. 6 shows a cross-sectional view of the piston assembly in FIG. 2.

The piston assembly (50), as shown in FIG. 2 and in greater detail in FIG. 6, has a main body (51) arranged around a central longitudinal axis (52). The main body (51) comprises an interior cavity (53) which is also longitudinal and is delimited by an interior wall (54). The main body (51) further comprises at least one interior clipping surface (55) arranged radially or transversely. In the embodiment shown, the piston assembly specifically contains two interior clipping surfaces (55). More specifically, the main body (51) presents an exterior, ring-shaped surface (56), arranged around the interior cavity (53) and oriented towards the handle assembly (30), and from which two elastic posts (57) extend. The elastic posts (57) have a transversely flexible trunk (58) and a head (59), the trunk (58) and head (59) generally forming a T-shape. The head (59) has an upper oblique part (60), which may be conical, curved or a combination thereof, and which is substantially hemispherical in the present embodiment; in its lower area, the head (59) has a lower transverse part on each side of the trunk (58), whereby one of these lower transverse parts provides the interior clipping surface (55) and the other of these lower transverse parts provides an exterior clipping surface (61).

Figure 8:
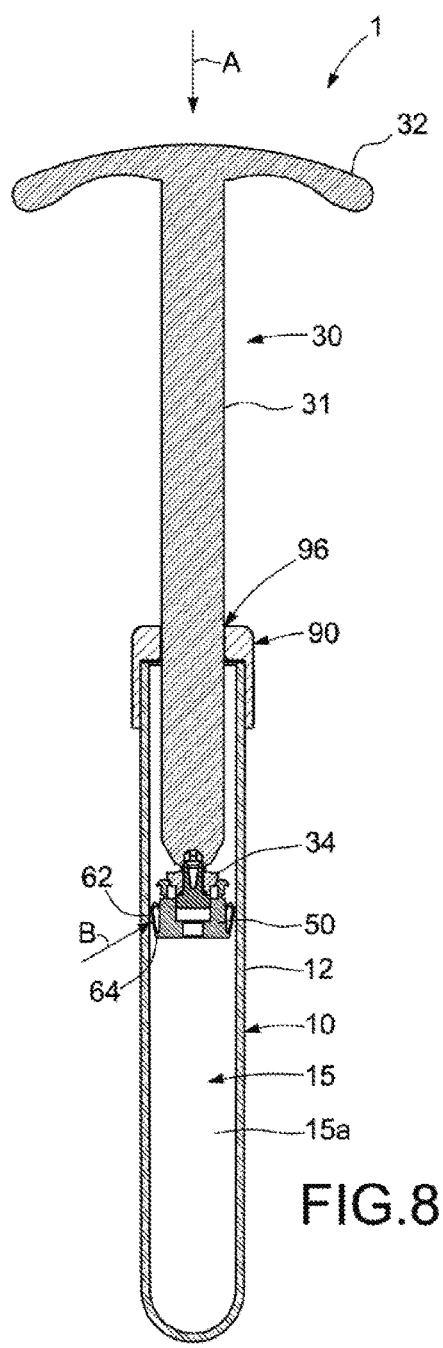
FIG. 8 shows a cross-sectional view of the device of FIG. 1 in a second situation, in which the handle assembly, the sealing element and the piston assembly have been inserted inside the tube and the cap has been attached to the tube.

As shown in FIG. 8, a space (15a) is delimited between the piston assembly (50) and the distal end (13) of the tube (10). The piston assembly (50) is movable along the interior cavity (15) of the tube (10) and in contact with the lateral wall (12) of the tube (10). As the piston assembly (50) sealingly moves along the interior cavity (15) and towards the proximal end (14), a depression is formed in the space (15a) between the piston assembly (50) and the distal end (13) of the tube (10). To provide the sealed contact, the piston assembly (50) of the present embodiment comprises an elastic skirt (62), which is shown more clearly in FIG. 6. This skirt (62) extends rearwards from a connecting portion (64) at an end portion of the main body (51), and is elastic so that it can pivot laterally inward and outward about the connecting portion (64), which functions like a hinge. As will be described hereinafter, by elastically and radially opening, the skirt (62) can sealingly adjust against the lateral wall (12) of the tube (10).

Figure 4:
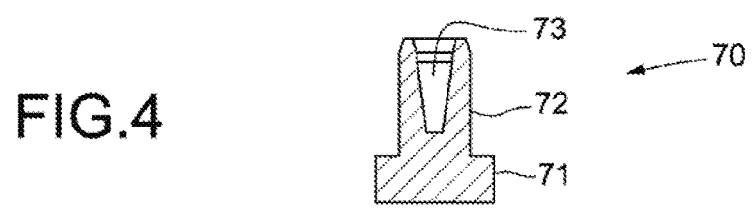
FIG. 4 shows a cross-sectional view of the perforable sealing element of in FIG. 2.

The perforable sealing element (70), visible in FIG. 2 and in greater detail in FIG. 4, has a disc-shaped head (71), and a trunk (72) that is narrower than the head (71) and which extends along the head (71) in the longitudinal direction. An interior cavity (73) is formed in the trunk (72), practically along the entire length thereof; in the embodiment depicted herein, for example, the interior cavity (73) covers more than three quarters of the length of the trunk (72).

Figure 5:
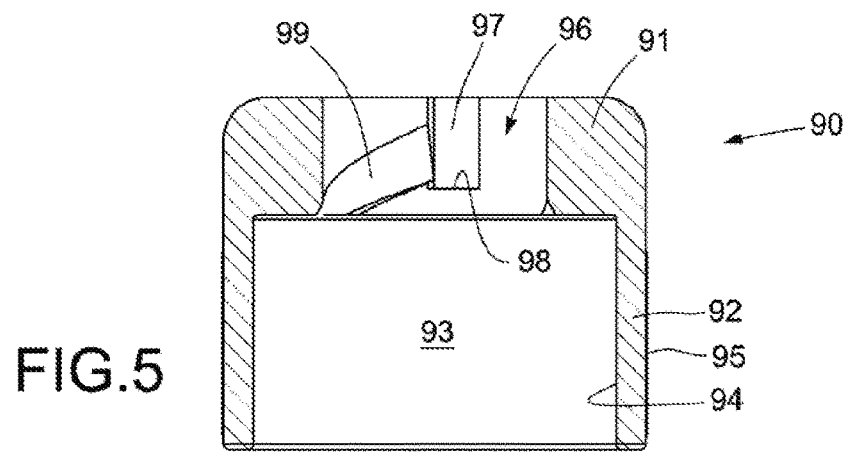
FIG. 5 shows a cross-sectional view of the cap of FIG. 2.

The cap (90), visible in FIG. 2 and in greater detail in FIG. 5, comprises a transverse wall (91) and a lateral wall (92), between which an interior space (93) is delimited. The lateral wall (92) has an interior surface (94) and an exterior surface (95). The interior space (93) and the interior surface (94) are adapted in size and shape to receive the proximal end (14) of the tube (10); for example, in the present embodiment, the interior surface (94) is cylindrical and has a diameter slightly larger than the external diameter of the tube (10) to enable the cap (90) to be easily yet snugly fitted on the tube (10). An orifice (96) is provided in the transverse wall (91), the orifice (96) being communicated with the interior space (93). The elongated body (31) of the handle assembly (30) passes through the orifice (96) and the interior space (93), as is explained in greater detail hereinafter. The orifice (96) is generally cylindrical, and comprises at least one radial recess (97) that provides a transverse seating surface or clipping surface (98). This radial recess (97) is communicated with the interior space (93) by a helical channel (99).

FIGS. 7 to 20 show a sequence of operation of the device (1) as per the invention, in which the different components of the device (1) are assembled and vacuum conditions are created inside the device (1).

FIG. 7 illustrates an initial step in which the cap is placed (90) on the handle assembly (30), inserting the end portion (34) and the elongated body (31) of the handle assembly (30) through the orifice (96) and the interior space (93) of the cap (90). The perforable sealing element (70) is coupled to the end portion (34) of the handle assembly (30), specifically by inserting the trunk (72) and part of the head (71) of the perforable sealing element (70) in the longitudinal interior cavity (35) of said end portion (34). Then, the piston assembly (50) is placed close to the end portion (34) and the perforable sealing element (70).

Then, as shown in FIG. 8, the end portion (34) of the handle assembly (30), the perforable sealing element (70) and the piston assembly (50) are inserted into the interior cavity (15) of the tube (10), via the opening (16), and the cap (90) is secured to the tube (10). In the present embodiment, for example, the tube (10) include an exterior thread (17), visible in FIGS. 2 and 7, to which a corresponding thread (not shown) of the interior surface (94) of the lateral wall (92) of the cap (90) is attached. Once the cap (90) has been attached, the size of the orifice (96) in the cap being relatively adjusted to the elongated body (31) of the handle assembly (30) prevents the handle assembly (30) from being removed from the tube (10). Then, by exerting a pushing force on the gripping portion (32) of the handle assembly (30) towards the tube (10) as indicated by the arrow (A), the set made up of the handle assembly (30), the piston assembly (50) and the perforable sealing element (70) overcomes the friction between the piston assembly (50) and the lateral wall (12) of the tube (10) and moves towards the bottom of the interior cavity (15) of the tube (10). As the piston assembly (50) moves towards the distal end (13) of the tube (10), there is an increase in the air pressure in the space (15a) in front of the piston assembly (50). This pressure increase causes the pressure in front of the piston assembly (50) to be greater than behind the piston assembly (50); because of this, inward forces are exerted on the skirt (62) of the piston assembly (50), as indicated by arrow (B). Consequently, the skirt (62) pivots slightly inwards with respect to the connecting portion (64), and gaps are formed between the skirt (62) and the lateral wall (12) of the tube (10), enabling air from the space (15a) to pass through these gaps and therefore the piston assembly (50) to be able to move forward.

Figure 9:
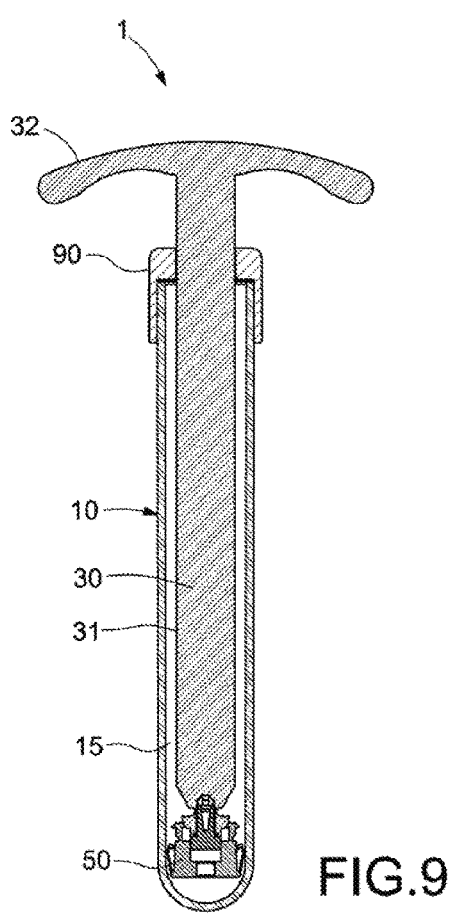
FIG. 9 shows a cross-sectional view of the device of FIG. 1 in a third situation, in which the handle assembly, the piston assembly and the perforable sealing element have been pushed to the bottom of the tube.
Figure 10:
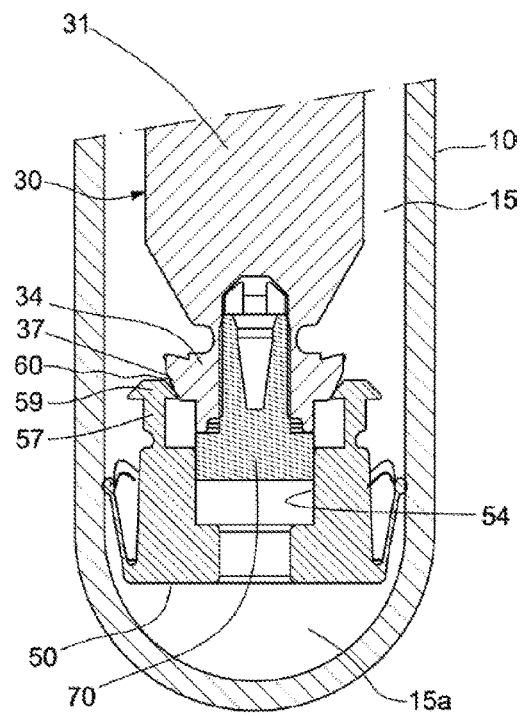
FIG. 10 shows an enlarged view of the piston assembly, the perforable sealing element and the end portion of the handle assembly in the situation of FIG. 9.

Continued application of force allows to reach the situation of FIG. 9, in which the piston assembly (50) reaches the bottom of the interior cavity (15) of the tube (10) and cannot advance any further. FIG. 10 shows an enlarged view of the piston assembly (50) in this situation. As shown, until this moment, the end portion (34) of the handle assembly (30) has pushed the piston assembly (50) to the bottom of the tube (10) by the lateral surface (37) of the end portion (34) of the handle assembly (30) exerting a force on the upper part (60) of the head (59) of the corresponding elastic post (57) of the piston assembly (50), and by the perforable sealing element (70) exerting a force against the interior wall (54) of the piston assembly (50) equal to the friction force between the perforable sealing element (70) and the interior wall (54) of the piston assembly (50).

Figure 11:
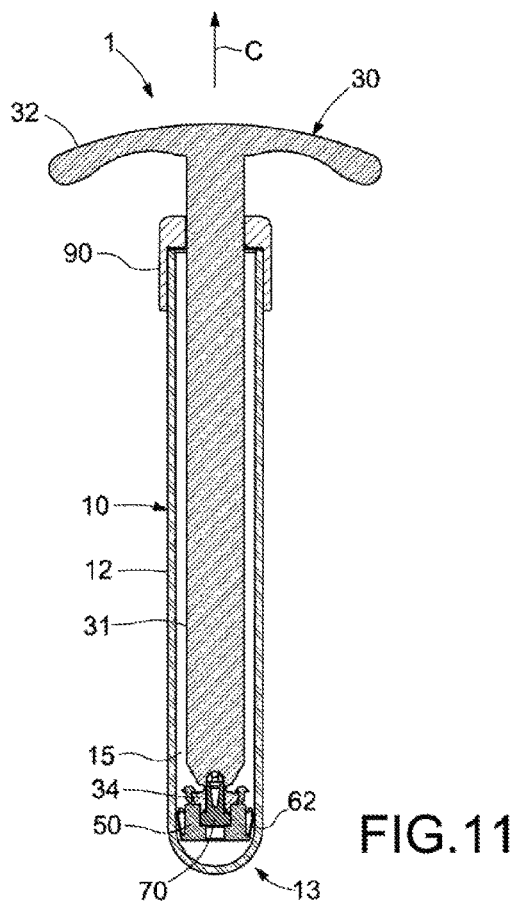
FIG. 11 shows a cross-sectional view of the device in FIG. 1 in a fourth situation, in which the handle assembly has been pushed, causing the handle assembly to clip to the piston assembly, and the perforable sealing element to reach a final position ensuring the sealing.
Figure 12:
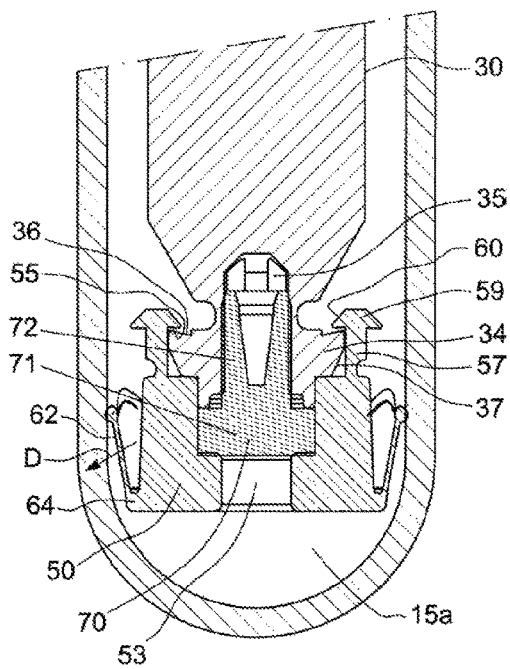
FIG. 12 shows an enlarged view of the piston assembly, the perforable sealing element and the end portion of the handle assembly in the situation of FIG. 11.

From the situation of FIGS. 9 and 10, if a sufficient pushing force is exerted on the gripping portion (32) of the handle assembly (30) towards the tube (10), the situation in FIGS. 11 and 12 is reached, in which the end portion (34) of the handle assembly (30) becomes clipped to the piston assembly (50). More specifically, as shown more clearly if observing a sequence formed by FIGS. 10 and 12, if a sufficient pushing force is exerted, the handle assembly (30) advances with respect to the piston assembly (50)—which cannot be moved as it has reached the bottom of the interior cavity (15)—, and the lateral surface (37) of the end portion (34) pushes the upper part (60) of the head (59) of the corresponding elastic post (57). Due to the fact that the lateral surface (37) and the upper part (60) are oblique, the longitudinal push of the lateral surface (37) causes the elastic posts (57) to open transversely; in consequence, the end portion (34) of the handle assembly (30) can overcome the head (59) of the elastic posts (57) and reach the situation of FIGS. 11 and 12, in which the clipping surface (36) of the end portion (34) comes into contact with the corresponding clipping surface interior (55) of the piston assembly (50) preventing the extraction of the end portion (34) of the piston assembly (50). In this situation, the perforable sealing element (70) remains in a final position which prevents the flow of fluid through the interior cavity (53) of the piston assembly (50) and the longitudinal interior cavity (35) of the end portion (34) of the handle assembly (30), specifically by the head (71) and part of the trunk (72) of the piston assembly blocking the flow of fluid. Furthermore, in this situation, as shown en FIG. 11, the gripping portion (32) of the handle assembly (30) remains accessible from outside the device (1).

from the clipped situation of FIGS. 11 and 12, the device (1) continues to be prepared by pulling the gripping portion (32) of the handle assembly (30) rearwards as indicated by arrow (C), causing the handle assembly (30) to begin moving back along the interior cavity (15) of the tube (10) guided by the cap (90). Due to the fact that the piston assembly (50) is clipped to the end portion (34) of the handle assembly (30), the piston assembly (50) and the perforable sealing element (70) move rearwards along with the handle assembly (30). The rearward moving of the piston assembly (50) causes a depression in the interior cavity (15) of the tube (10) between the piston assembly (50) and the distal end (13) of the tube (10). This depression causes the resultant force exerted on the skirt (62) by the air that is in front of and behind the piston assembly (50) to be directed outwards as indicated by arrow (D). This outward force causing the skirt (62) to remain pivoted against the lateral wall (12) of the tube (10). This contact creates a seal against the lateral wall (12) that prevents the flow of air around the piston assembly (50).

Figure 15:
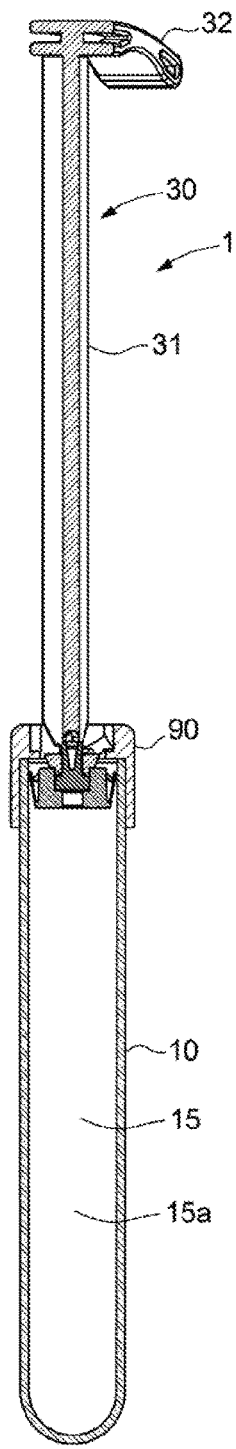
FIG. 15 shows a cross-sectional view of the device of FIG. 1 in the fifth situation, taken along a section plane that is perpendicular to the section plane of FIG. 13.
Figure 16:
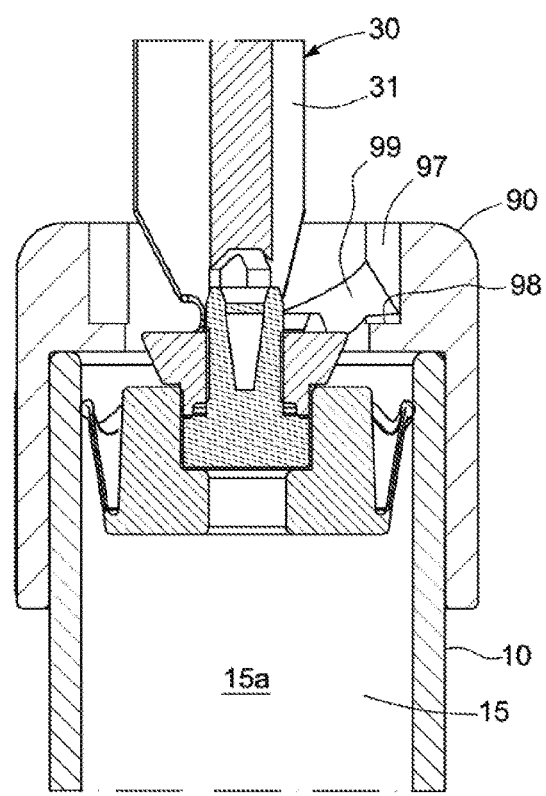
FIG. 16 shows an enlarged view of the piston assembly, the perforable sealing element, the end portion of the handle assembly and the cap of FIG. 15.
Figure 19:
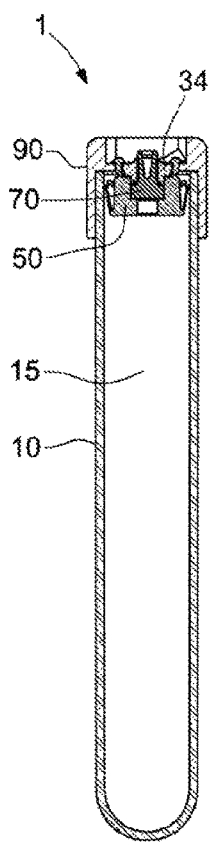
FIG. 19 shows a cross-sectional view of the device of FIG. 1 in a seventh situation, in which the handle assembly has been broken at the separable area, and the entire handle assembly has been removed with the exception of the end portion, thereby obtaining a perforable vacuum container suitable for vacuum-drawing blood or for another application.

The rearward movement of the piston assembly (50) ends when the situation shown in FIGS. 13 and 14 is reached, in which the head (59) of the elastic posts (57) comes into contact with the transverse wall (91) of the cap (90). At this time, the head (59) of each elastic post (57) is located at the beginning of a respective helical channel (99) of the cap (90). FIGS. 15 and 16 show two sectional views of the device (1) in the same situation as FIGS. 13 and 14, but having made the section with the section plane that forms a 90° angle with the section plane corresponding to FIGS. 13 and 14. FIGS. 15 and 16 show that the helical channel (99) ends in the radial recess (97), where the clipping surface (98) is located.

From the situation of FIGS. 13 to 16, the user continues pulling the gripping portion (32) of the handle assembly (30) whilst turning this gripping portion (32)—and thus the entire handle assembly (30)—in a clockwise direction. In consequence, the heads (59) of the elastic posts (57) penetrate the corresponding helical channels (99) of the cap (90), and the set made up of the handle assembly (30), the piston assembly (50) and the perforable sealing element (70) moves rearwards slightly and also turns with respect to the longitudinal axis (11) of the tube (10) as the heads (59) of the elastic posts (57) rise up the respective helical channels (99). Because the space (15a) is at a reduced pressure due to the effect of the rearward movement of the piston assembly (50), the pressing and sealing of the skirt (62) against the lateral wall (12) of the tube (10) is maintained.

When the user has turned the gripping portion (32) approximately 90° in a clockwise direction, the piston assembly (50) reaches a second rotational position shown in FIGS. 17 and 18. In this situation or second rotational position, the head (59) of each elastic post (57) has reached a radial recess (97) of the cap (90) and the outer clipping surface (61) of each head (59) has come into contact and lies against the clipping surface (98) of the corresponding radial recess (97). In consequence, the end portion (34) of the handle assembly (30) is clipped to the piston assembly (50) in such a way that it cannot move rearwards towards the exterior of the tube (10), and the piston assembly (50) is clipped to the cap (90) in such a way that it cannot move towards the interior of the tube (10). In turn, optimum depression conditions are available within the space (15a) between the piston assembly (50) and the distal end (13) of the tube (10), guaranteed by the sealing contact of the piston assembly (50) against the lateral wall (12) of the tube (10).

Having reached this vacuumed and clipped situation, the user breaks the handle assembly (30) at the separable area (33), for instance by pulling and/or further rotating the gripping portion (32). The user then removes the elongated body (31) and the gripping portion (32) of the handle assembly (30), reaching the situation shown in FIGS. 19 and 20. As shown, the invention has allowed obtaining a final container or tube that, similarly to a conventional precharged vacuum tube, has an interior space (15a) with reduced pressure or vacuum conditions, and is permanently closed at one end (the distal end (13)) whilst the other end (14) has a sealed, perforable closure. This sealed, perforable closure is provided by the assembly formed by the cap (90), the piston assembly (50), the perforable sealing element (70) and the end portion (34)—which remains clipped to the piston assembly (50)—. In this final situation, the piston assembly (50) cannot move forwards or rearwards along the tube (10) as it is clipped to the cap (90).

However, unlike a pre-charged conventional vacuum tube, the vacuum conditions of the tube as per the invention at the time of its use are optimum. In the container of the present invention, the vacuum conditions are created at the time of its use, via the simple operation explained in the previous paragraphs. Once the handle assembly has been separated, there remains a tube similar to conventional tubes, which can be used to collect blood drawn from a person or animal, placed in a centrifugal machine, placed in a tube carrier stand, etc.

In the present embodiment, the handle assembly (30) is formed as a single piece, for example integrally injected in plastic, and the separable area (33) of the handle assembly (30) is a breakable area, which simplifies the manufacture of the handle assembly (30). As shown in FIG. 3, to facilitate this breakage, the separable area (33) of the handle assembly (30) may have a smaller transverse dimension than the end portion (34) of the handle assembly (30). For example, the separable area (33) of the present embodiment is an indentation or area with a reduced diameter. Furthermore, in the present embodiment, the longitudinal interior cavity (35) of the end portion (34) extends along the whole of the separable area (33). This enables the thickness of the walls of the separable area (33) to be minimised and therefore the separable area (33) to be broken relatively easily.

Furthermore, as shown, for example, in FIG. 18, the perforable sealing element (70) of the present embodiment is arranged inside the longitudinal interior cavity (35) of the end portion (34) of the handle assembly (30), and along the separable area (33). This means that, although the walls of the separable area (33) are thin, the effective thickness of the set made up of the handle assembly (30) and the perforable sealing element (70) at the separable area (33) is increased and therefore the separable area (33) does not break when the steps prior to the breaking of the handle assembly (30) are being carried out (steps in FIGS. 7 to 18).

Figure 20:
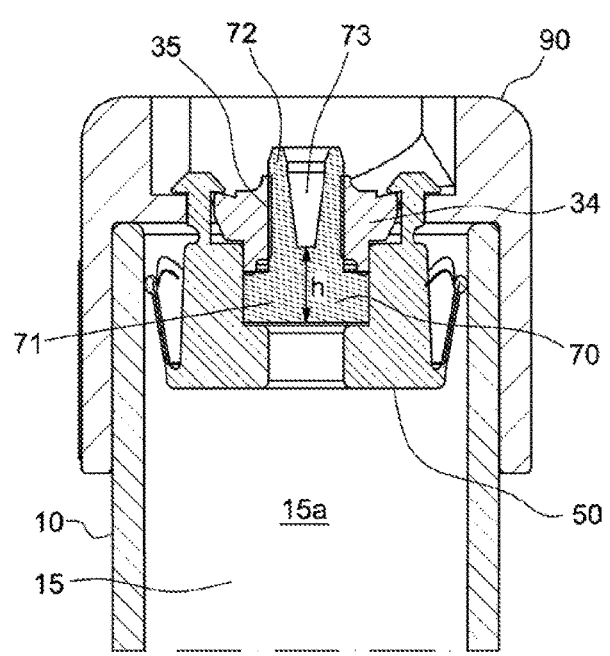
FIG. 20 shows an enlarged view of the piston assembly, the perforable sealing element, the end portion of the handle assembly and the cap in the situation of FIG. 19.

FIG. 20 illustrates that the presence of the interior cavity (73) of the perforable sealing element (70) allows minimising the thickness or height (h) of the layer of sealant material in a longitudinal direction and in the central area of the perforable sealing element (70), whilst ensuring that the total height of the perforable sealing element (70) remains high in order to carry out the reinforcement functions explained in the previous paragraphs. In this way, the insertion of a needle through this central area is facilitated when the device is used to collect blood or other compound.

In the present embodiment, as shown in FIG. 3, the clipping surface (36) of the distal end (13) of the handle assembly (30) is arranged continuously along a perimeter around a central longitudinal axis of the distal end (13). This enables the handle assembly (30) to be clipped to the piston assembly (50) in any rotational position.

Preferably, as shown in FIG. 6, the elastic skirt (62) of the piston assembly (50) has an increasing width; for example, in the embodiment shown, the skirt (62) is conical. This enables the skirt (62) to be adjusted against the lateral wall (12) of the tube (10) regardless of whether the wall of the tube (10) is perfectly cylindrical or slightly conical or presents another slight variation in shape. Furthermore, in the present embodiment, the skirt (62) has an undulated outer contour (63), which favours the sealed adjustment of the skirt against the lateral wall (12) of the tube (10). This undulated shape is less rigid when moving through the interior of the tube when the interior wall (12) has a conical surface. Therefore, the material of the piston assembly (50) does not have to fulfil as many requirements and can be less sophisticated.

FIGS. 21 to 24 show a second embodiment of a device (100) as per the invention, which is generally the same as the previous embodiment, including the fact that the device (100) comprises a handle assembly (130) which includes an elongated body (131), a gripping portion (132), a separable area (133) and an end portion (134), wherein the latter has a longitudinal interior cavity (135) and at least one clipping surface (136). However, as shown in FIGS. 21 and 22, the device (100) as per the invention differs to the embodiment in FIGS. 1 to 20 in that the gripping portion (132) and the end portion (134) of the handle assembly (130) are two separate pieces and in that the separable area (133) is an clipping or clipped union between the gripping portion (132) and the end portion (134), wherein the clipped union can be unclipped.

Figures 23, 24:
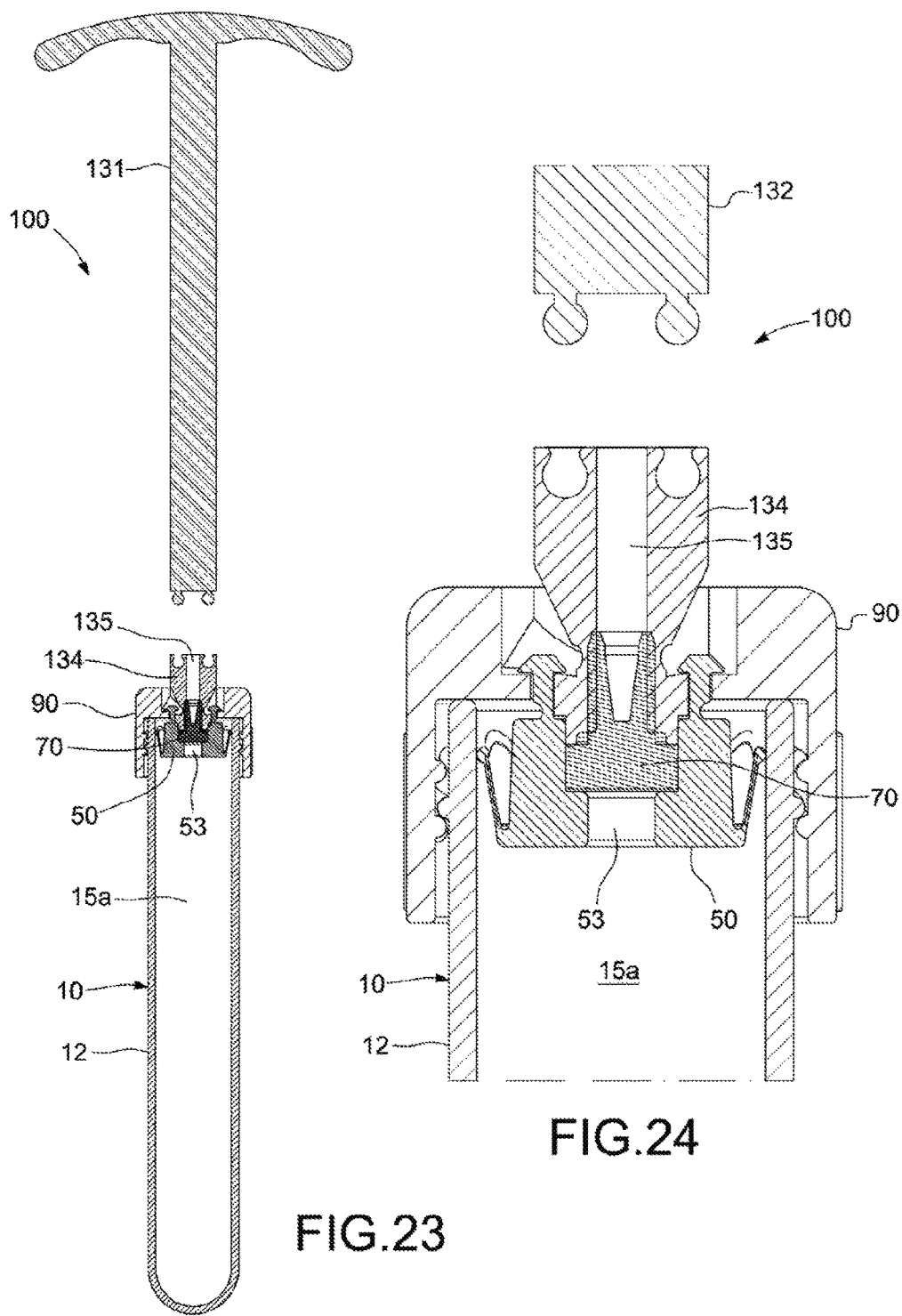
FIG. 23 shows a cross-sectional view of the device of FIG. 21, in a subsequent situation in which most of the handle assembly has been unclipped and removed, obtaining a perforable vacuum container suitable for vacuum-drawing blood or for another application.
FIG. 24 shows an enlarged view of the piston assembly, the perforable sealing element, the separable area and end portion of the handle assembly, and the cap in the situation of FIG. 23.

FIGS. 21 and 22 show the device (100) in a similar situation to that in FIG. 17, i.e. in which the handle assembly (130) has been pulled rearwards and turned in a clockwise direction, causing the piston assembly (50) to become clipped to the cap (90) in the same way as the previous embodiment. Then, if the user exerts sufficient traction force on the gripping portion (132) of the handle assembly (130), the situation shown in FIGS. 23 and 24 is reached, in which the clipped union of the separable area (133) is unclipped and the gripping portion (132) is separated from the end portion (134) of the handle assembly (134). Once more, a container has been obtained that has a vacuum space (15a) delimited by a tube (12) closed by a cap (90) and a piston assembly (50) clipped to the cap (90), wherein this space (15a) is separated from the exterior by a perforable element (70). Under these conditions, the tube can be used to extract blood, to centrifuge blood, or in other applications. To access this space (15a), a needle can be inserted through the longitudinal interior cavity (135) of the end portion (134), the perforable element (70) and the interior cavity (53) of the piston assembly (50), providing fluid communication for a fluid to flow through them.

Figure 25:
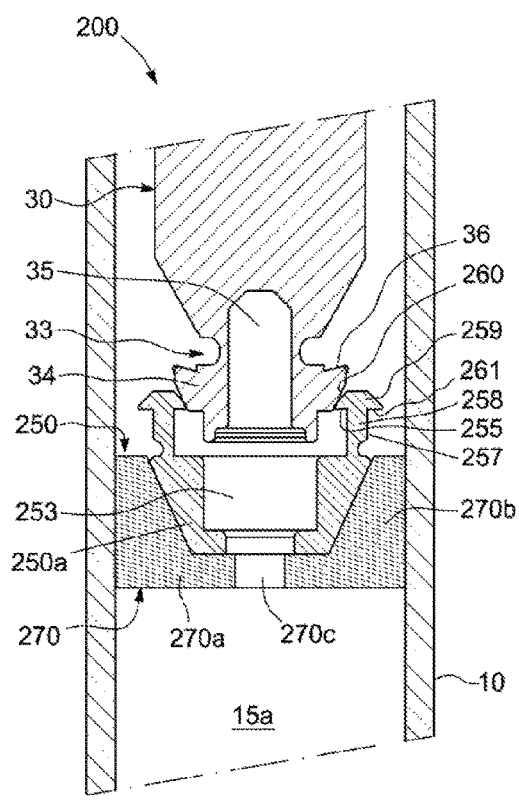
FIG. 25 shows an enlarged view of a third embodiment of the device as per the invention, in a situation in which the end portion of the handle assembly has not yet been clipped to the piston assembly.
Figure 26:
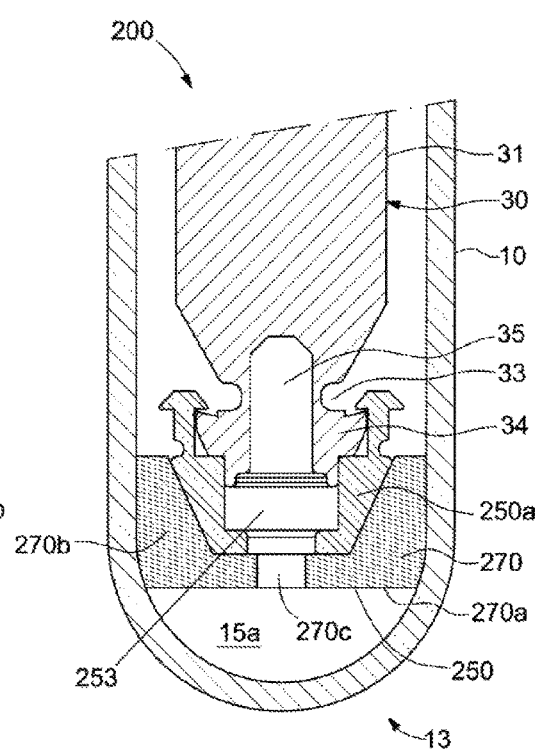
FIG. 26 shows the device of FIG. 25, in a subsequent situation in which the end portion of the handle assembly has been clipped to the piston assembly.

FIGS. 25 and 26 show a third embodiment of a device (200) as per the invention, wherein the device (200) of the present embodiment has a tube (10), a cap (90)—not shown—, a piston assembly (250) fitted with an interior cavity (253) for the flow of fluid, a perforable sealing element (270) to seal a space (15a) inside the tube (10), and a handle assembly (30) accessible from the outside to move the piston assembly (250) as in the previous embodiments. Furthermore, similarly to the device (100) of the first embodiment, the handle assembly (30) of the present embodiment is made of a single piece and with a breakable separable area (33); the end portion (34) of the handle assembly (30) also has a longitudinal interior cavity (35).

However, the present device (200) differs from the previous embodiments in that the perforable sealing element (270) forms part of the piston assembly (250), i.e. moves together with the piston assembly (250) at all times. Furthermore, the piston assembly (250) comprises an interior element (250a), which comprises the interior cavity (253) of the piston assembly (250). In the present embodiment, the perforable sealing element (270) is exterior, and comprises a transverse exterior cap (270a) and an exterior wall (270b)

that extends from the exterior cap (270a) and surrounds a portion of the interior element (250a). The exterior cap (270a) has an orifice (270c) aligned with the interior cavity (253). As shown in FIG. 25, when the piston assembly (250) moves towards the distal end (13) of the tube (10) without the handle assembly (30) having been clipped to the piston assembly (250), the air in the space (15a) is expelled through the orifice (270c) and the interior cavity (253), enabling the movement of the piston assembly (250) towards the bottom of the tube (10). As shown in FIG. 26, once the piston assembly (250) has reached the bottom of the tube (10) and the handle assembly (30) has been clipped to the piston assembly (250), the end portion (34) of the handle assembly (30) is partially introduced into the interior cavity (253), sealing it and preventing air from being expelled from the space (15a) via the orifice (270c) and the interior cavity (253). From the clipped situation in FIG. 26, if the handle assembly (30) is pulled and the piston assembly (250) is moved rearwards, a depression is formed in the space (15a).

In certain embodiments, the interior element (250a) may be rigid to provide the piston assembly (250) with greater robustness, whilst the elastic exterior perforable sealing element (270) ensures sealed contact against the wall (12) of the tube (10).

In alternative embodiments, the interior element (250a) may be slightly smaller than the end portion (34) of the handle assembly (30), so that when the end portion (34) is clipped to the interior element (250a), the interior element (250a) expands elastically, pushing the perforable sealing element (270) outwards, enhancing the sealed contact against the wall (12) of the tube (10). This allows the contact between the piston assembly (250) and the wall of the tube (10) to be less when the handle assembly (30) is being pushed towards the interior of the tube (10), and to be greater when the handle assembly (30) and the piston assembly (250) have been clipped and the handle assembly (30) is pulled rearwards to create the vacuum. This effect may facilitate use of the device, as less force needs to be exerted to push the handle assembly (30) towards the interior of the tube (10).

Figure 27:
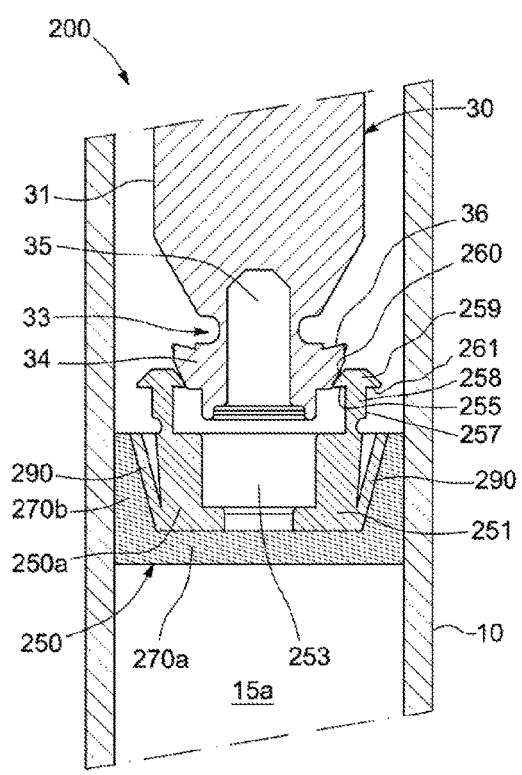
FIG. 27 shows an enlarged view of a fourth embodiment of the device as per the invention, in a situation in which the end portion of the handle assembly has not yet been clipped to the piston assembly.
Figure 28:
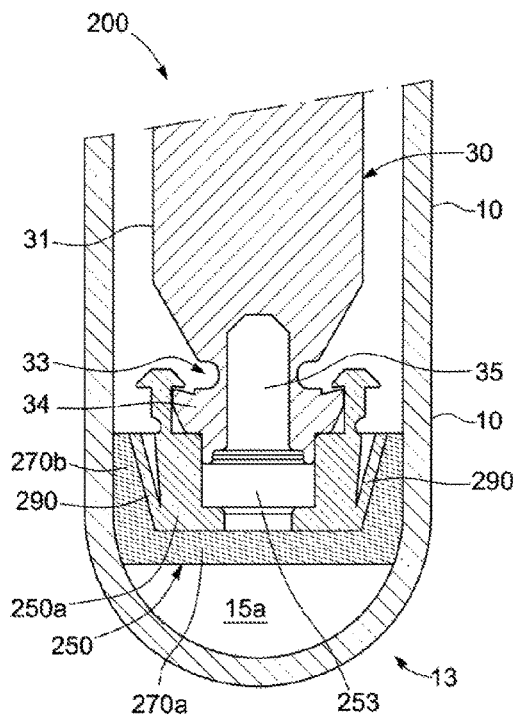
FIG. 28 shows the device of FIG. 27, in a subsequent situation in which the end portion of the handle assembly has been clipped to the piston assembly.

FIGS. 27 and 28 show a variation of the previous embodiment, illustrated in similar situations to those of FIGS. 25 and 26. In the present embodiment of FIGS. 27 and 28, the exterior cap (270a) does not have an orifice. In addition, at least the part of the interior element (250a) of the piston assembly (250) which is surrounded by the exterior wall (270b) of the perforable sealing element (270) applies an elastic push against the exterior wall (270b) of the sealing element (270). More specifically, in the present embodiment, this elastic push is exerted by lateral elastic arms (290), which are inserted deformed into the perforable sealing element (270) so that they tend to open elastically (pushing radially outwards) and therefore widen the perforable sealing element (270) and contribute to the sealed contact between the exterior wall (270b) of the sealing element (270) and the lateral wall (12) of the tube (10). In other words, the lateral elastic arms (290) and the exterior wall (270b) present a combined function similar to the pivotable elastic skirt (62) of the embodiments of FIGS. 1 to 24.

Figure 29:
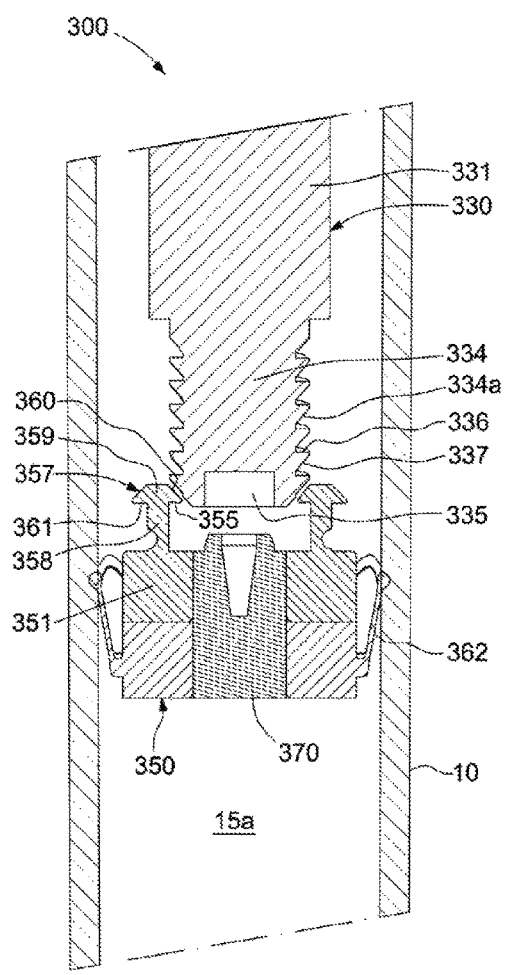
FIG. 29 shows an enlarged view of a fifth embodiment of the device as per the invention, in a situation in which the handle assembly has not yet been clipped to the piston assembly.
Figure 30:
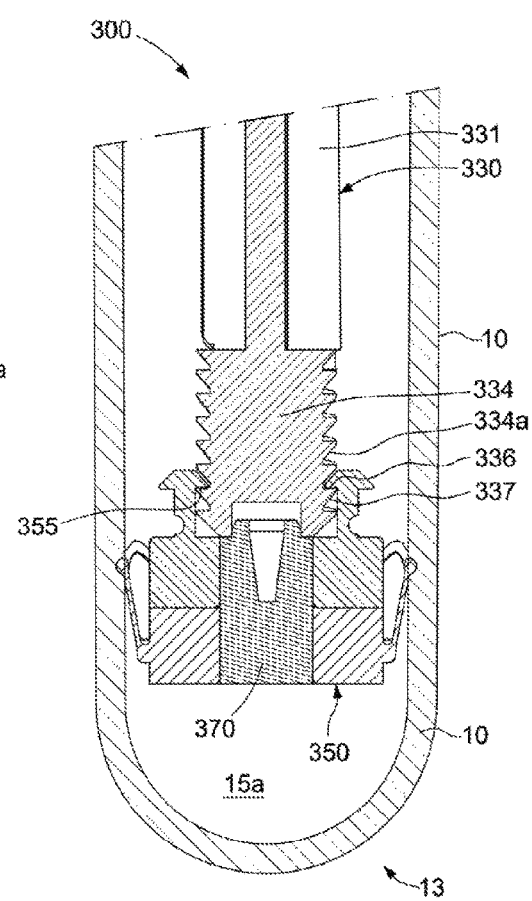
FIG. 30 shows the device of FIG. 29, in a subsequent situation in which the end portion of the handle assembly has been clipped to the piston assembly.

FIGS. 29 and 30 show a device (300) in accordance with an alternative embodiment. This device (300) comprises a handle assembly (330) and a piston assembly (350) that are movable inside a tube (10). The handle assembly (330) has an elongated body (331), a gripping portion or handle—not shown—, and an end portion (334) that is threaded, i.e. fitted with an exterior threaded profile (334a). The end portion (334) has a longitudinal interior cavity (335), at least one clipping surface (336) intended to be clipped to the piston assembly (350), and at least one oblique lateral surface (337) with an increasing width towards the clipping surface (336), which helps to cause clipping in a similar way to the previous embodiments. The clipping surface (336) and the lateral surface (337) of the present embodiment form part of the exterior threaded profile (334a). The piston assembly (350), in turn, is formed of a first piece (351) provided with elastic posts (357) similar to the previous embodiment; these elastic posts (357) comprise an interior clipping surface (355) and an exterior clipping surface (361), intended to be clipped to a clipping surface (336) and to the cap—not shown—similarly to previous embodiments. The piston assembly (350) of the present embodiment has a skirt (362) that functions similarly to the skirt (62) of the first embodiment described in this document.

The pushing and clipping of the present embodiment takes place differently to the previous embodiments. On one hand, as illustrated in FIG. 29, the piston assembly (350) can be pushed along the tube (10) by the handle assembly (330) until reaching the bottom of the tube (10). If the handle assembly (330) is continued to be pushed with sufficient force, the lateral conical surfaces (337) push and deform the elastic posts (357) and the end portion (334) is inserted between the elastic posts (357), the end portion (334) becoming clipped by the contact between the clipping surfaces (336) and the interior clipping surfaces (355) of the elastic posts (357).

The separation of the handle assembly (300) from the piston assembly (350) occurs differently. Once the handle assembly (330) and the piston assembly (350) are moved rearwards and clipped to the cap (similarly to FIG. 18), the handle assembly (330) is unthreaded from the elastic posts (357) by turning the handle assembly (330) with respect to the piston assembly (350), which is prevented from rotating by the cap.

The present embodiment comprises a perforable sealing element (370) that forms part of the piston assembly (350). The rest of the piston assembly (350) can be made out of one or more pieces (the illustrated example has two) and one or more materials of variable rigidity.

Alternative embodiments are contemplated in which the configuration of the threaded handle assembly (300) described with reference to FIGS. 29 and 30 is used in combination with any other type of piston assembly (350) within the scope of the claims.

Alternative embodiments are contemplated in which the exact geometry of the parts that make up the clipping surfaces according to the claims may vary.

Alternative embodiments are contemplated in which partial vacuums can be formed, for which the handle assembly may have more than one separable area.

The tube of the present embodiment may be made out of glass, plastic or any other applicable material, and may or may not have a surface treatment.

Diverse marketing or presentation formats of the device are also contemplated. For example, the device may be presented fully or partially unassembled. Alternatively, the device may be presented in similar situations to that of FIG. 11 (which coincides with FIG. 1), i.e. with the handle assembly and the piston assembly inserted to the bottom of the tube and clipped to each other, so that the user only needs to unwrap the tube, pull the handle assembly rearwards, turn the handle assembly and separate the handle assembly (e.g. by breaking or unclipping) to obtain a tube with an optimum vacuum ready for use.

It is also contemplated that the device can be marketed with the tube (10) in an empty condition, i.e. not containing any additives (for instance, any coagulant substances, anti-coagulant substances, etc.). Alternatively, the tube (10) can be marketed containing an additive. For instance, the tube (10) can be marketed containing at least one pro-coagulant. It is also contemplated that the tube (10) can have superficial properties given by the materials of which the tube (10) is made from, or by the geometry of the internal walls of the tube (10). For instance, the tube (10) can be manufactured from glass, silicone, kaonilite, cerite or bentonite. The inner wall of the tube (10) can be treated with ionized gas in order to accelerate the coagulation of a blood plasma contained in the tube (10) when the tube (10) is in use. The internal surface can have a rugosity that allows accelerating the coagulation of said plasma. The pro-coagulant superficial properties can be present along all or part of the internal wall surface of the tube (10). Using a pro-coagulant tube (10) allows to accelerate the coagulation of a plasma contained in the tube (10) in circumstances in which such acceleration may be convenient for a surgical or medical technique using a final plasma-derived composition.

It is also contemplated that the tube (10) can have anti-coagulant superficial properties given by the materials of which to the tube (10) is manufactured or by the geometry of the internal walls of the tube (10). For instance, the tube (10) can be manufactured from or coated with hydrophobic polymers such as polyethylene, polypropylene, polytetrafluoroethylene, polyvinylchloride, polyethylene terephthalate, polysiloxane, polystyrene, polycarbonate, cyclic olefin copolymer. The internal surface of the tube (10) can be treated with ionized gas to produce hydrophobic properties. Using an anti-coagulant tube (10) allows to delay the coagulation of blood or plasma contained in the tube (10) in circumstances in which such delay is convenient for a surgical or medical technique using a composition prepared by means of the tube (10). Delaying the blood coagulation allows to increase the wait time before centrifuging the plasma, if necessary. The anti-coagulant properties can be present along all or part of the internal wall surface of the tube (10); this aspect also has an effect on the delay in coagulation.

The invention claimed is:

1. A device for the extraction of blood or a blood compound, comprising:
   a tube that extends along a longitudinal axis and which has a lateral wall, a closed distal end, a proximal end opposite the distal end and an interior cavity communicated with an exterior by an opening at the proximal end;
   a piston assembly that is movable along the interior cavity of the tube, the piston assembly delimiting a space between the piston assembly and the distal end of the tube;
   a handle assembly, having a gripping portion and an end portion, and
   a perforable sealing element;
   wherein the device is configured to adopt an advancing position in which the handle assembly pushes the piston assembly towards the distal end and is not clipped to the piston assembly, and in which air in the space is expelled through the piston assembly and/or via a space between the piston assembly and the lateral wall of the tube; and
   wherein the device is configured to adopt a retreating position in which the end portion of the handle assembly is clipped to the piston assembly and pulls the piston assembly towards the proximal end and in which the piston assembly and the perforable sealing element seal the space between the piston assembly and the distal end of the tube.

2. The device, in accordance with claim 1, wherein the piston assembly has a main body from which a skirt extends rearwards, wherein the skirt is elastic and flexible and has an increasing width.

3. The device, in accordance with claim 2, wherein the skirt has an undulated outer contour.

4. The device, in accordance with claim 1, wherein the piston assembly comprises at least one interior clipping surface, and the end portion has at least one clipping surface, wherein the interior clipping surface of the piston assembly hooks to the clipping surface of the end portion.

5. The device, in accordance with claim 4, wherein the clipping surface of the end portion is arranged continuously around perimeter of a longitudinal axis of the handle assembly.

6. The device, in accordance with claim 1, wherein the piston assembly further comprises at least one exterior clipping surface, and the device further comprises a cap that is fixed to the proximal end of the tube and which has an orifice through which the handle assembly protrudes from the tube, wherein the cap comprises at least one clipping surface against which an exterior clipping surface of the piston assembly comes into contact when the handle assembly and the piston assembly are arranged in an extended position with respect to the tube, preventing the advancement of the piston assembly and the handle assembly towards a more compressed position with respect to the tube.

7. The device, in accordance with claim 6, wherein the piston assembly is rotatable with respect to the tube and the cap, and adopts a first rotational position in which there is no contact between the exterior clipping surface of the piston assembly and the clipping surface of the cap and in which the piston assembly is longitudinally movable with respect to the cap, and a second rotational position in which there is contact between the exterior clipping surface of the piston assembly and a clipping surface of the cap and a longitudinal movement of the piston assembly towards the interior of the tube is prevented.

8. The device, in accordance with claim 7, wherein the piston assembly moves longitudinally to pass from the first rotational position to the second rotational position.

9. The device, in accordance with claim 6, wherein the piston assembly has a main body from which one or more elastic posts extend longitudinally, wherein the elastic posts are fitted with a transversely flexible trunk and a head, the trunk and the head forming a T-shape with an oblique upper part and a lower transverse part extending radially on each side of the trunk, the lower transverse parts providing the exterior clipping surface and an interior clipping surface.

10. The device, in accordance with claim 1, wherein a perforable sealing element is arranged inside a longitudinal interior cavity provided in the end portion of the handle assembly and in a separable area.

11. The device, in accordance with claim 1, wherein the handle assembly has a separable area, wherein the end portion extends from the separable area, and wherein the end portion configured to be separated from the rest of the handle assembly at the separable area.

12. The device, in accordance with claim 11, wherein the separable area is breakable.

13. The device, in accordance with claim 12, wherein the separable area of the handle assembly has a smaller transverse dimension than the end portion of the handle assembly, and a longitudinal interior cavity of the end portion extends along the separable area.

14. The device, in accordance with claim 11, wherein the separable area comprises a clipping that can be unclipped.

15. The device, in accordance with claim 1, wherein the perforable sealing element is comprised in the piston assembly, and the piston assembly further comprises an interior element, wherein the perforable sealing element comprises a transverse exterior cap.

16. The device, in accordance with claim 15, wherein the transverse exterior cap blocks the flow of fluid between the space and the distal end of the tube.

17. The device, in accordance with claim 15, wherein the transverse exterior cap comprises a through orifice communicated with an interior cavity of the piston assembly, wherein, in the advancing position, the orifice and the interior cavity provide a space for the passing of air through the piston assembly, and wherein, in the retreating position, the end portion blocks the flow of fluid through the piston assembly.

18. The device, in accordance with claim 15, wherein the perforable sealing element further comprises an exterior wall that extends from the exterior cap and surrounds a portion of the interior element, the exterior wall remaining between the interior element and the lateral wall of the tube and in sealed contact with the lateral wall when the device is in the retreating position.

19. The device, in accordance with claim 18, wherein the perforable sealing element is elastic, and at least the portion of the interior element that is surrounded by the exterior wall of the perforable sealing element applies an elastic push against the exterior wall of the sealing element contributing to the sealed contact between the exterior wall of the sealing element and the lateral wall of the tube when the device is in the retreating position.

20. The device, in accordance with claim 18, wherein the end portion of the handle assembly has a greater transverse dimension than the interior cavity of the interior element, and in the clipped position, the end portion is at least partially housed in the interior cavity and pushes the interior element radially outwards.

21. The device, in accordance with claim 1, wherein the end portion has an exterior threaded profile, configured to be clipped to the piston assembly in the retreating position, and to unthread from the piston assembly after a clipped position has been achieved.

* * * * *